United States Patent
Brown et al.

(10) Patent No.: US 9,438,981 B2
(45) Date of Patent: Sep. 6, 2016

(54) MRI COMPATIBLE HEADSET

(71) Applicant: NeoCoil, LLC, Pewaukee, WI (US)

(72) Inventors: Brian Brown, Wauwatosa, WI (US); Manuel J. Ferrer Herrera, West Bend, WI (US); Richard J. Smaglick, New Berlin, WI (US)

(73) Assignee: NeoCoil, LLC, Pewaukee, WI (US)

( * ) Notice: Subject to any disclaimer, the term of this patent is extended or adjusted under 35 U.S.C. 154(b) by 0 days.

(21) Appl. No.: 14/989,478

(22) Filed: Jan. 6, 2016

(65) Prior Publication Data

US 2016/0119704 A1 Apr. 28, 2016

Related U.S. Application Data

(62) Division of application No. 13/491,650, filed on Jun. 8, 2012, now Pat. No. 9,264,793.

(60) Provisional application No. 61/648,876, filed on May 18, 2012.

(51) Int. Cl.
| | |
|---|---|
| *H04R 25/00* | (2006.01) |
| *H04R 1/10* | (2006.01) |
| *H04R 5/033* | (2006.01) |
| *G10L 21/0272* | (2013.01) |
| *A61B 5/055* | (2006.01) |

(52) U.S. Cl.
CPC ......... *H04R 1/1016* (2013.01); *G10L 21/0272* (2013.01); *H04R 1/1033* (2013.01); *H04R 1/1091* (2013.01); *H04R 5/033* (2013.01); *A61B 5/055* (2013.01); *H04R 2420/07* (2013.01)

(58) Field of Classification Search
CPC H04R 1/1091; H04R 2420/07; H04R 5/033; A61B 5/055
See application file for complete search history.

(56) References Cited

U.S. PATENT DOCUMENTS

| | | |
|---|---|---|
| 5,277,184 A | 1/1994 | Messana |
| 7,292,704 B2 | 11/2007 | Lederer |
| 7,609,844 B2 | 10/2009 | Lederer |
| 8,103,014 B2 | 1/2012 | Porzelt et al. |
| 2009/0123112 A1 | 5/2009 | Kahana et al. |
| 2009/0185699 A1 | 7/2009 | Kim |
| 2012/0083717 A1 | 4/2012 | Alleman et al. |
| 2013/0311176 A1* | 11/2013 | Brown ................. H04R 1/1091 704/233 |

(Continued)

OTHER PUBLICATIONS

Magnacoustics Genesis Ultra; "Communication & Music System for MRI"—(2 pages).
Resonance Technology Inc.; "SereneSound", "SereneSound's State-of-the-Art Headset and Transducer"—(2 pages).
Optoacoustics, Ltd.; "IMROC Interventional MR Optical Communication System",—(3 pages).
Nordic Neurolab; "AudioSystem High-end audio solution for fMRI";—(2 pages).

*Primary Examiner* — Tuan D Nguyen
(74) *Attorney, Agent, or Firm* — Boyle Fredrickson, S.C.

(57) ABSTRACT

A wireless headset capable of receiving audio signals transmitted wirelessly and compatible for use in an MRI scanner is disclosed. The headset includes a first wireless module connected to the first earphone and a second wireless module connected to the second earphone. Each wireless module is electrically connected to a speaker in the respective earphone. The first wireless module receives the audio signal from a remote source and coordinates transmission of the audio signal to each of the speakers. The compact nature of each earphone minimizes the length of wire runs. In addition, the headset is made of materials having low magnetic susceptibility such that they will not be affected by the magnetic field from the MRI scanner.

20 Claims, 5 Drawing Sheets

(56) References Cited

U.S. PATENT DOCUMENTS

2014/0275970 A1\* 9/2014 Brown ............... G01R 33/3692
600/413

2014/0354283 A1\* 12/2014 Kwon .................. G01R 33/283
324/322

\* cited by examiner

MRI COMPATIBLE HEADSET

CROSS-REFERENCE TO RELATED APPLICATIONS

This application is a divisional application of U.S. Ser. No. 13/491,650, filed on Jun. 8, 2012, which, in turn, claims priority to U.S. provisional application Ser. No. 61/648,876, filed May 18, 2012, the entire contents of each application is incorporated herein by reference.

BACKGROUND OF THE INVENTION

The subject matter disclosed herein relates to magnetic resonance imaging (MRI) compatible headphones. More specifically, headphones suitable for use by a patient in an MRI scanner are disclosed.

As is known to those skilled in the art, an MRI system alternately generates a strong magnetic field and then detects the faint nuclear magnetic resonance (NMR) signals given off by nuclei in the presence of the magnetic field. The NMR signals are received by antennas, also known as coils, and transmitted to the MRI scanner for reconstruction into an MRI image. In order to provide a clear image, it is desirable to minimize electromagnetic interference from outside sources.

Figure 9:
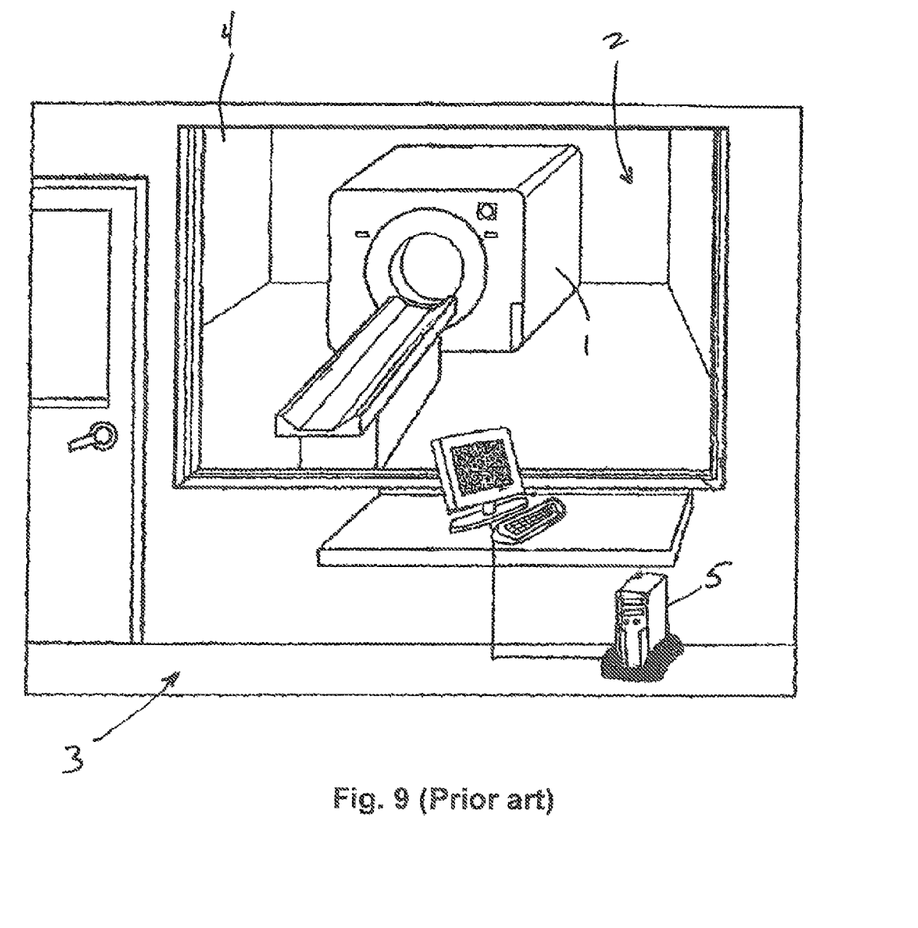
FIG. 9 is an illustration of an exemplary MRI scan room and control room.

As a result, MRI scanners 1 are located within a shielded room 2, also known as the scan room (see FIG. 9). The scan room 2 includes walls, or panels, which typically incorporate RF shielding within the wall. The controller 5 for the MRI scanner 1 is typically located in an adjacent control room 3. A window 4 permits an operator to observe activity within the scan room 2 from the adjacent control room 3. The operator often needs to communicate with the patient, for example, to provide instructions to the patient during the scan. Consequently, a microphone may be provided in the control room for the operator and a headset provided to the patient to receive instructions from the MRI operator.

However, the MRI environment creates numerous challenges that make conventional electronic headsets unusable in the MRI environment. Most commercial headsets utilize a magnetic speaker driver and may include one or more other components that are susceptible to magnetic fields. The magnetic field generated by the MRI scanner may, at a minimum, interfere with these devices, and at worst, pull the devices into the bore of the scanner, potentially injuring the patient. Further, non-magnetic metal components may be susceptible to radio frequency (RF) induced heating. Also, long wire runs, for example, between the control room and the patient or even between earphones function as antennas. These long wire runs raise the potential of both radiating electromagnetic interference detectable by the MRI scanner due to audio signals transmitted on the wire and receiving interference from the MRI scanner which degrades the audio signal provided to the patient.

Historically, these limitations of conventional electronic headsets have been overcome by providing pneumatic headsets to the patient. However, such a system is not without drawbacks. The pneumatic headsets require a dedicated controller to convert an electronic audio signal to a pneumatic audio signal for transmission to the patient. Pneumatic tubing extending from this controller to the patient is also required.

BRIEF DESCRIPTION OF THE INVENTION

The subject matter disclosed herein describes a wireless headset capable of receiving audio signals transmitted wirelessly and compatible for use in an MRI scanner. The headset includes a first wireless module connected to the first earphone and a second wireless module connected to the second earphone. Each wireless module is electrically connected to a speaker in the respective earphone. The first wireless module receives an audio signal from a remote source and coordinates transmission of the audio signal to each of the speakers. The compact nature of each earphone minimizes the length of wire runs. Further, wireless communications between earphones eliminates a wire extending between the earphones. In addition, the headset is made of materials having low magnetic susceptibility such that they will not be affected by the magnetic field from the MRI scanner.

According to a first embodiment of the invention, a headset for a patient to wirelessly receive an audio signal during a magnetic resonance image (MRI) scan includes a first earphone, a second earphone, and a headband having a first end and a second end. The first earphone is connected proximate to the first end and the second earphone is connected proximate to the second end. The first earphone includes a first wireless audio module configured to receive the audio signal and to wirelessly retransmit at least a portion of the audio signal and a first speaker electrically connected to the first wireless audio module and configured to reproduce at least a portion of the audio signal. The second earphone includes a second wireless audio module configured to receive the portion of the audio signal retransmitted from the first wireless audio module and a second speaker electrically connected to the second wireless audio module and configured to reproduce the portion of the audio signal received by the second wireless audio module. Each of the components of the headset is made of materials having low magnetic susceptibility.

According to another aspect of the invention, the first earphone may further include a first proximity sensor having a detection range and the second earphone may further include a second proximity sensor having a detection range. Each proximity sensor is configured to generate a signal corresponding to the presence of an object within the detection range. Each of the first and second wireless audio modules are configurable to operate in a first operating mode or a second operating mode as a function of the signal generated by the first and the second proximity sensors, respectively. The audio signal may be a stereo signal. The first wireless audio module transfers a first channel of the audio signal to the first speaker, and the first wireless audio module wirelessly retransmits a second channel of the audio signal to the second wireless audio module. The second wireless audio module transfers the second channel of the audio signal to the second speaker.

According to yet another aspect of the invention, the first earphone may further include at least one first microphone configured to detect audio signals proximate to the first earphone and generate a first signal corresponding to the audio signals proximate to the first earphone. The first wireless audio module is further configured to receive the first signal corresponding to the audio signals proximate to the first earphone, generate a first audio signal that cancels at least a portion of the audio signals proximate to the first earphone, and transfer the first audio signal that cancels at least a portion of the audio signals to the first speaker. The second earphone may further include at least one second microphone configured to detect audio signals proximate to the second earphone and generate a second signal corresponding to the audio signals proximate to the second earphone. The second wireless audio module is further configured to receive the second signal corresponding to the audio signals proximate to the second earphone, generate a second audio signal that cancels at least a portion of the ambient audio signals proximate to the second earphone, and transfer the second audio signal that cancels at least a portion of the ambient audio signals to the second speaker.

According to still another aspect of the invention, the headset may include a support arm having a first end and a second end. The first end of the support arm is connected to one of the first end or the second end of the headband, and a microphone is mounted proximate the second end of the support arm. The microphone is configured to receive the patient's voice and transfer a signal to either the first or second wireless audio modules. The first or second wireless audio module is configured to wirelessly transmit the signal received from the microphone. The microphone also receives ambient noise along with the patient's voice. The first or second wireless audio module is configured to process the signal to separate the patient's voice from the ambient noise, generate an audio signal that cancels at least a portion of the ambient audio signals, and add the audio signal that cancels at least a portion of the ambient audio signals to the signal received from the microphone prior to wirelessly transmitting the signal.

According to another embodiment of the invention, an MRI compatible headset for receiving a wireless audio signal includes a first earphone and a second earphone. The first earphone includes a wireless audio module, a signal processing device, and a first speaker. The wireless audio module is configured to receive the wireless audio signal and output a wired audio signal. The signal processing device is configured to receive the wired audio signal and to process the wired audio signal into a first channel signal and a second channel signal. The first speaker is configured to receive the first channel signal and reproduce the first channel signal as an audio output. The second earphone includes a second speaker configured to receive the second channel signal and reproduce the second channel signal as an audio output. The headset further includes a transmission means for transmitting the second channel signal between the signal processing device and the second speaker. Each of the components of the headset are made of materials having low magnetic susceptibility.

According to another aspect of the invention, the transmission means includes an electrical conductor connected between the first and second earphones and at least one cable trap connected in series with the electrical conductor. The cable trap is configured to reduce currents induced by magnetic fields during an MRI scan. Optionally, the transmission means includes an optical transceiver in the first earphone, an optical transceiver in the second earphone, and an optical fiber connecting the optical transceiver to the optical transceiver. As still another option, the transmission means includes a second wireless audio module in the second earphone, and the wireless audio module in the first earphone is configured to retransmit the second channel signal to the second wireless audio module.

These and other objects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWING(S)

Various exemplary embodiments of the subject matter disclosed herein are illustrated in the accompanying drawings in which like reference numerals represent like parts throughout, and in which.

In describing the preferred embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements where such connection is recognized as being equivalent by those skilled in the art.

DETAILED DESCRIPTION OF THE PREFERRED EMBODIMENTS

The various features and advantageous details of the subject matter disclosed herein are explained more fully with reference to the non-limiting embodiments described in detail in the following description.

Referring initially to FIGS. 1-4, one embodiment of an MRI compatible headset 10 is illustrated. The headset 10 includes a first earphone 40 and a second earphone 50. A headband 12 extends between the first earphone 40 and the second earphone 50. The headband includes a first end 16 and a second end 18 and includes a curved portion 17 configured to fit a patient's head. Optionally, the length of the headband 12 may be adjustable to adjust to varying sizes of patient's heads. The first earphone 40 is mounted to the headband 12 at a first mounting connection 20 proximate to the first end 16 of the headband 12, and the second earphone 50 is mounted to the headband 12 at a second mounting connection 22 proximate to the second end of the headband 12. Each mounting connection 20, 22 may provide a rigid mount or a pivotal mount between the earphone 40, 50 and the headband 12. A pivotal mount allowing each earphone 40, 50 to more comfortably engage the patient's ear. The headset 10 may also include a foam pad 30 or any other suitable cushioned material to improve patient comfort. An outer surface 34 of the foam pad 30 is mounted to an inner surface 14 of the headband 12. The inner surface 32 of the foam pad 30 is configured to engage the patient's head.

Each of the components of the headset are constructed of materials having low magnetic susceptibility and low magnetic signature. Magnetic susceptibility is a physical property of materials which identifies to what degree the material is affected by an applied magnetic field. If a material has high magnetic susceptibility, it is affected more significantly by an applied magnetic field, becoming magnetized itself and being attracted to the source of the applied magnetic field. If the applied magnetic field is strong enough and the material has a sufficiently high magnetic susceptibility, an object may be drawn toward the source of the applied magnetic field. Conversely, materials with low magnetic susceptibility are relatively unaffected by an applied magnetic field. These materials either do not become magnetized or are magnetized in such a minor degree as they will not be drawn toward the source of the applied magnetic field. As is understood in the art, MRI scanners generate magnetic fields having uniform field density and having a field strength ranging, for example, from 0.5-3 Tesla. As used herein, a material having low magnetic susceptibility will not be drawn toward the magnetic field generated by the scanner. A material having a low magnetic signature will not distort the uniform field to a degree that it would create an artifact in an MRI image.

Figure 7:
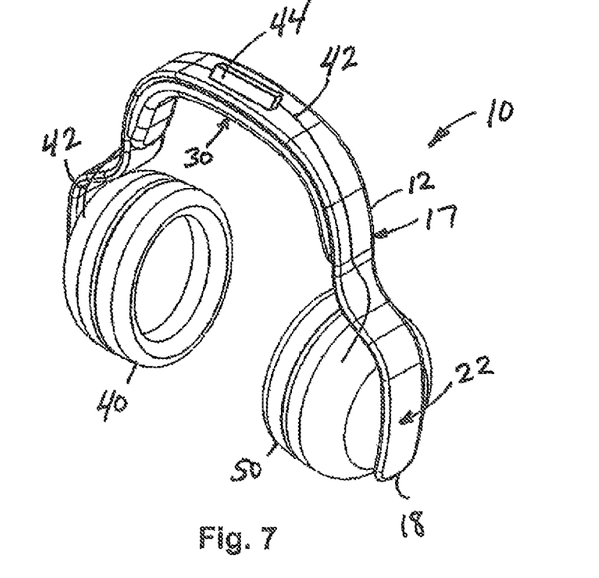
FIG. 7 is a perspective view of a headset according to another embodiment of the invention.
Figure 8:
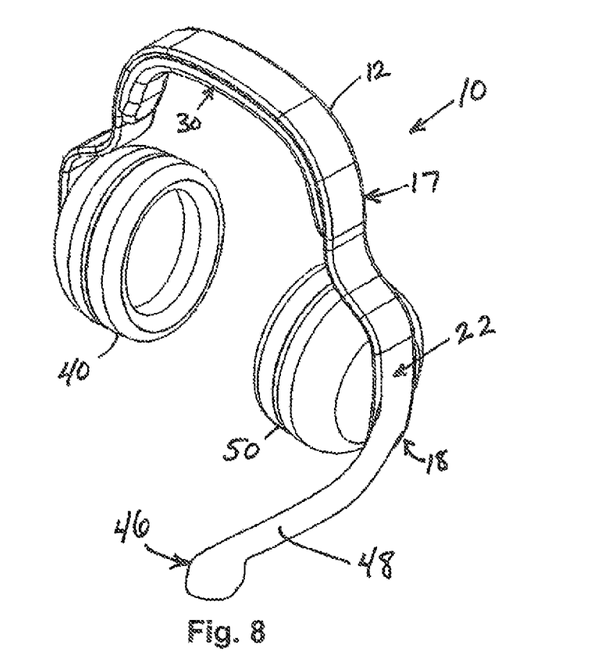
FIG. 8 is a perspective view of a headset according to another embodiment of the invention.

It is contemplated that the headset 10 may include other configurations without deviating from the scope of the invention. According to other embodiments of the invention, each earphone 40, 50 may include a clip to hook behind a patient's ear to secure the earphone to the patient. The earphone 40, 50 may a bud-style earphone, configured to engage a patient's ear canal rather than fit over the ear. Referring also to FIG. 7, the headset 10 may include a wire 42 extending between the first earphone 40 and the second earphone 50. The wire 42 may be a fiber-optic cable, providing a conductive path for photons to be passed between the two earphones 40, 50. Optionally, the wire 42 may be electrically conductive and further include one or more cable traps 44 connected in series with the wire 42. The cable trap 44 is configured to reduce currents induced in the wire 42 from MRI gradients thereby reducing distortion of the audio signal transferred in the wire 42 and inductive heating of the wire 42. MRI scanners typically operate at frequencies in the megahertz, for example, in a range between 60 MHz and 150 MHz. Therefore, the cable traps may be configured to reduce signals having a similar range of frequencies. Referring also to FIG. 8, the headset 10 may include a microphone 46 mounted to an arm 48 extending from either the first end 16 or the second end 18 of the headband 12. The arm 48 may be movably mounted such that the microphone 46 may be positioned proximate to the patient's mouth. Optionally, the microphone 46 may be mounted directly to one of the earphones 40, 50. The headset 10 may be realized according to various combinations and arrangements of the above-described embodiments.

Figure 1:
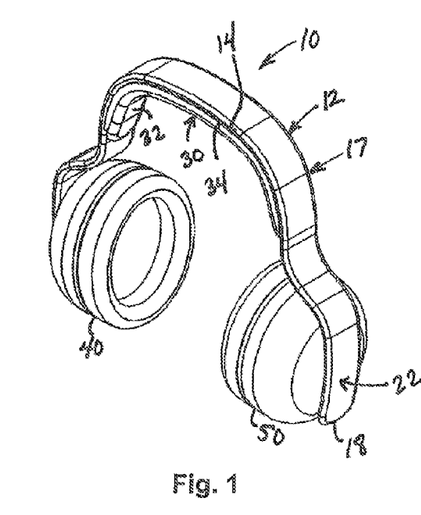
FIG. 1 is a perspective view of a headset according to one embodiment of the invention.
Figure 2:
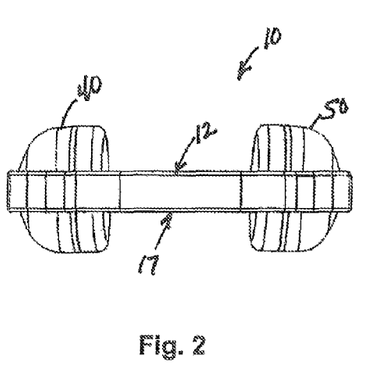
FIG. 2 is a top plan view of the headset of FIG. 1.
Figure 3:
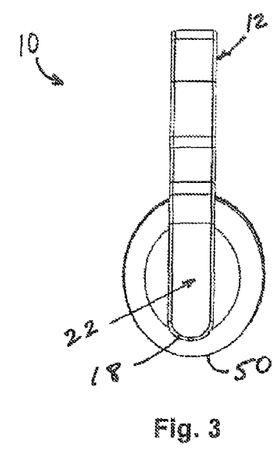
FIG. 3 is a side elevation view of the headset of FIG. 1.
Figure 4:
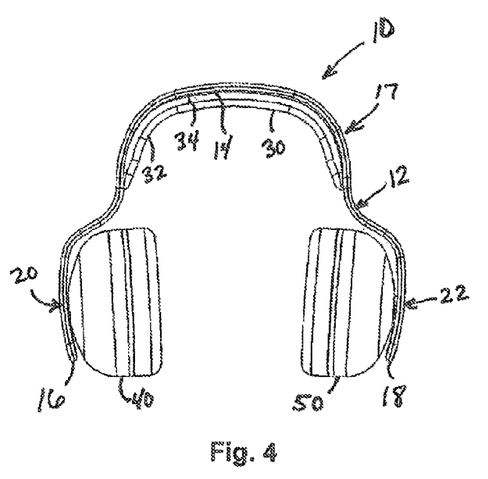
FIG. 4 is a front elevation view of the headset of FIG. 1.
Figure 5:
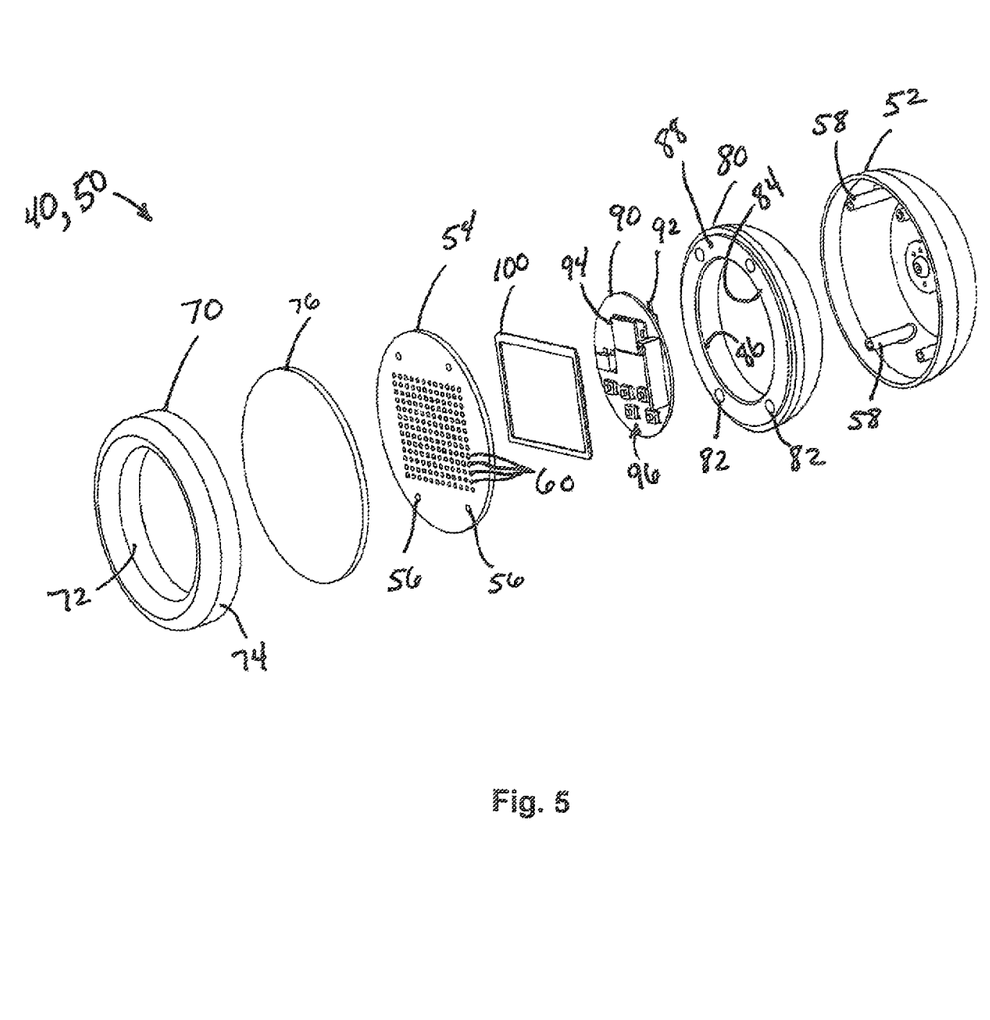
FIG. 5 is a partial exploded view of one of the earphones from the headset of FIG. 1.

Referring next to FIG. 5, an exploded view of one of the earphones 40, 50 of FIG. 1 includes a rear housing 52 and a front housing 54. The front housing 54 includes multiple mounting holes 56 configured to align with mounting posts 58 in the rear housing 52. A fastener such as a screw or a bolt is inserted through each mounting hole 56 and engages the mounting post 58 to positively retain the front housing 54 to the rear housing 52. The front housing 54 includes a plurality of holes 60 to facilitate sound waves from a speaker 100 within the housing to travel through the front housing 54. The speaker 100 is of a low magnetic susceptibility construction, including, but not limited to a piezoelectric speaker or an electrostatic speaker. Optionally, the speaker 100 may include one or more speakers configured, for example, to reproduce specific frequency bands of an audio signal.

A cushion 70 is fitted to the front housing 54 and configured to engage the patient. The cushion 70 includes an opening 72 extending through the center to facilitate sound waves travelling from the housing to the patient's ear. An outer periphery 74 of the cushion 70 is greater than the outer periphery of the housing such that the cushion 70 may fit over the housing. According to one embodiment of the invention, the cushion 70 is attached to the housing by a friction fit, allowing the cushion 70 to be removed and replaced as needed. Optionally, the cushion 70 may be removably mounted to the housing by any other connector, such as a snap or hook and loop fastener. According to still another embodiment, the cushion 70 may be secured to the housing, for example, by an adhesive. The earphone 40, 50 may further include a cover 76 secured between the cushion 70 and the front housing 54. The cover 76 protects the earphone 40, 50 preventing dust and dirt from entering the holes 60 in the front housing 54 yet is made of a material that allows the transmission of the sound waves.

A spacer 80 is configured to fit within the rear housing 52. The spacer is shaped complementary to the rear housing 52 and includes passages 82 extending through the spacer 80 configured to receive the mounting posts 58. An opening 84 in the center of the spacer 80 includes an inner periphery 86. A raised portion 88 on the front face of the spacer 80 is offset from and extends around the inner periphery 86, defining a seat for a circuit board 90. The circuit board 90 is configured to engage the seat on the spacer 80 with a portion of the electronic components mounted to each side of the circuit board 90. The electronic components mounted on the side of the circuit board 90 engaging the spacer 80 fit within the opening 84 of the spacer, and the mounting posts 58 extend thorough the spacer 80 a sufficient distance to provide space for the electronic components mounted on the other side of the circuit board 90. The spacer 80 provides mechanical damping to the circuit board and speaker such that they resist vibration caused by acoustic resonance. As discussed below, the MRI scan room 2 is typically an acoustically noisy environment and, absent the mechanical damping, the magnitude of the noise could cause the components to resonate or vibrate, causing yet more noise proximate to the patient's ear.

Figure 6:
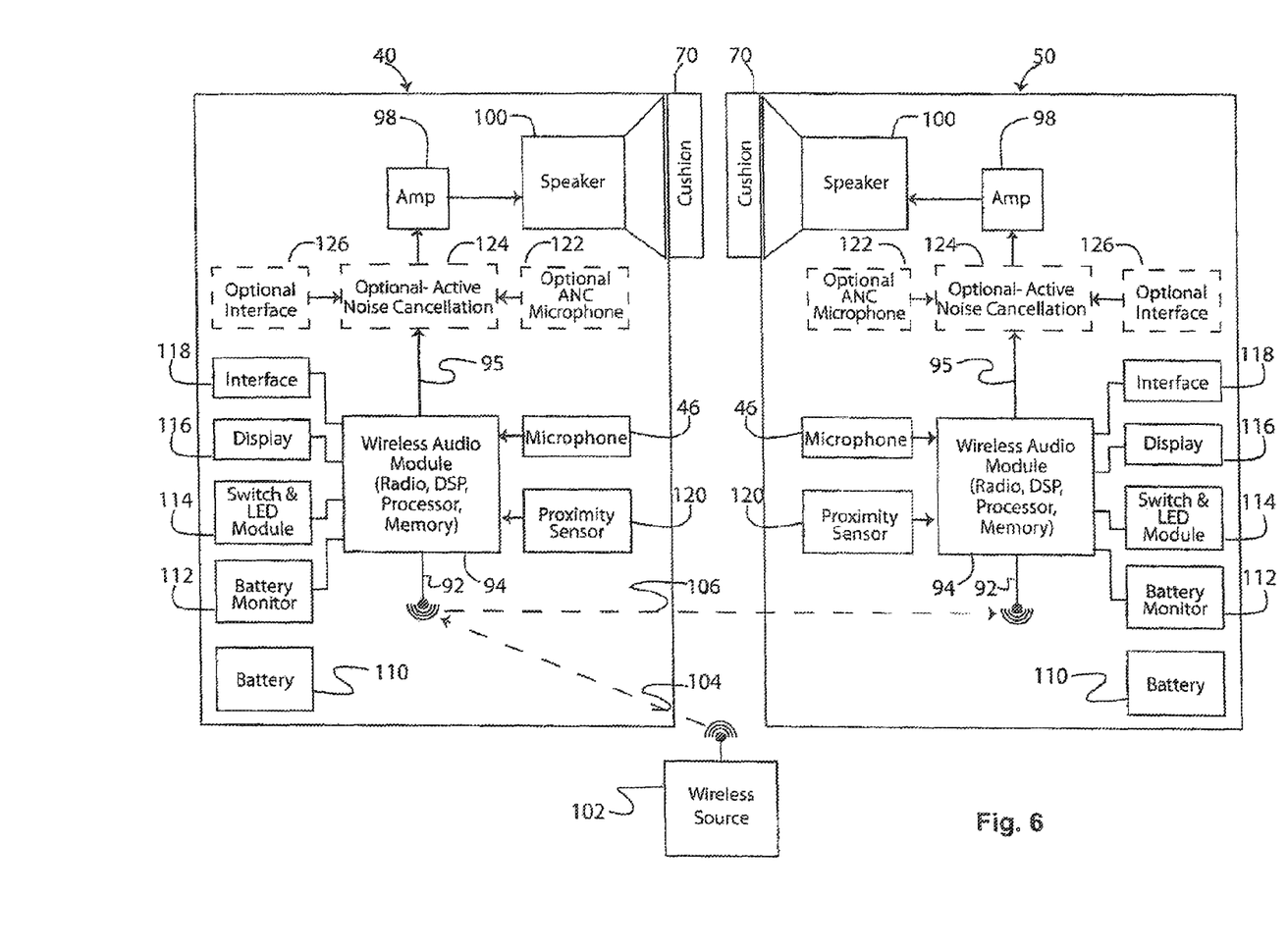
FIG. 6 is a block diagram representation of the headset according to one embodiment of the invention.

The electronic components on the circuit board are configured to convert a wireless audio signal to an audio output to the patient. Referring also to FIG. 6, an antenna 92 receives the wireless audio signal 104 from an external wireless source 102. The wireless audio signal 104 may be formatted according to any suitable wireless communication standard, for example, Bluetooth® or IEEE 802.11. The wireless audio signal 104 is provided to a wireless audio module 94. The wireless audio module 94 is a single integrated circuit including multiple functions, including, but not limited to radio frequency modulation and demodulation, digital signal processing, other processing, and storing data in on board or external memory. According to other embodiments of the invention, the functions of the wireless audio module 94 may be provided by individual processors or included in various combinations on one or more processors. An amplifier 98 is connected in series between the wireless audio module 94 and a speaker 100.

As used herein, a "wireless" signal is a radio frequency (RF) signal transmitted from an RF transmitter to an RF receiver where the RF transmitter and/or receiver may be discrete electronic components, a portion of an RF transceiver, or a portion of another module, which includes other features, for example processing of the RF signals, and any required supporting electronic circuitry.

Other electronic components 96 are illustrated generally on the circuit board 90 in FIG. 5 with exemplary components illustrated in block diagram form in FIG. 6. Each earphone 40, 50 may include a battery 110 and a battery monitor circuit 112. The battery monitor circuit 112 measures the voltage or current level on the battery to determine performance and/or an expected remaining life of the battery. The battery monitor circuit 112 generates a signal if the voltage or current level drops below a predetermined threshold to indicate, for example, low remaining life of the battery and may be provided to wireless audio module 94 and transmitted to the remote source 102 or be connected to a light emitting diode (LED) in the switch and LED module 114. Other switches and LEDs as required by the headset may include, but are not limited to a power switch, push-to-talk (PTT) switch, audio source selection switch, and corresponding LEDs indicating status of any of the afore mentioned switches or other operating conditions of the headset 10. Similarly, a display unit 116 may be included to provide a visual indication of the operating status or configuration status of the headset 10. A programming interface 118 allows new programs and/or configurations to be loaded into the wireless audio module 94 from a remote programming device. It is further contemplated that the earphone 40, 50 include a proximity sensor 120 to detect whether the earphone is being worn by a patient. Each earphone 40, 50 may additionally be configured to provide active noise cancellation (ANC). A dedicated processing device 124 along with a programming interface 126 for the ANC processing device 124 may be included. A microphone 122 transfers a signal to the ANC processing device corresponding to the sounds present proximate to the microphone 122.

The electronic components 96 are arranged on the circuit board 90 to reduce potential side effects detrimental to either the headset 10 or the MRI scanner. The electronic components 96 are located in close proximity to other components to which they are electrically connected, reducing the length of traces or wire runs between the components, thereby reducing the potential for heating due to currents induced on those traces or wire runs by the MRI scanner. The electronic components 96 are also arranged to minimize the formation of loops, which are susceptible to coupling with the magnetic field from the MRI scanner. Further, the electromagnetic shielding may be included on a portion of or on the entire circuit board 90 to reduce the interaction between the MRI scanner and the circuit board 90.

According to one embodiment of the invention, the headset 10 includes a first earphone 40 and a second earphone 50 having identical components with different programs stored in memory of each earphone 40, 50. Optionally, the same program may be stored in memory and each earphone 40, 50 includes a selector such as a jumper switch that selects whether the earphone 40, 50 is, for example, a left/right earphone or a master/follower earphone. According to another embodiment of the invention, the headset 10 includes a first earphone 40 and a second earphone 50 having different sets of components. Referring, for example, to FIGS. 7 and 8, a wire 42 (electrical or optical) may connect the two earphones 40, 50. One of the earphones 40, 50 may be configured to receive the wireless audio signal 104 and perform any required processing with a single wireless audio module 94. The wireless audio module 94 subsequently outputs the appropriate signal for each speaker 100 either internally to the earphone 40, 50 or via the wire 42 connecting the two earphones 40, 50. The other of the earphones 40, 50 may include just the speaker 100, the amplifier 98 and speaker 100, or any other subset of components according to the desired level of control provided in the second earphone 40, 50.

In operation, the headset 10 receives a wireless audio signal 104 from a remote source 102 and converts it to an audio signal to the patient. As illustrated in FIG. 6, each of the earphones 40, 50 include the same components. One of the two earphones 40, 50 operates as a master device and the other as a follower device in order to synchronize playback of the audio signal between the two speakers 100. Therefore, for purposes of illustration, the first earphone 40 will be referred to as the master and the second earphone 50 will be referred to as the follower.

The antenna 92 in the master earphone 40 receives the wireless audio signal 104 and transfers it to its respective wireless audio module 94. The wireless audio module 94 is configured to execute a program, or series of instructions, stored in memory. The wireless audio module 94 processes the wireless audio signal 104 to determine which portion 106 needs to be output from the speaker 100 in the follower earphone 50. This portion 106 of the wireless audio signal 104 may be the entire signal, for example, if a single channel signal is received, or one channel of the signal, if a dual channel signal is received. The master wireless audio module 94 then transmits this portion 106 of the wireless audio signal 104 to the follower wireless audio module 94 via the respective antennas 92. Each of the master and follower wireless audio modules 94 subsequently processes the respective signal 104, 106 received at that module 94 to provide an output signal 95 from the wireless audio module 94. This output signal 95 is subsequently converted by the respective amplifier 98 and speaker 100 to an audio signal to the patient.

The headset 10 is powered by at least one battery 110 having low magnetic susceptibility. Optionally, each earphone 40, 50 may include a separate battery 110. The battery 110 may be rechargeable or non-rechargeable. For either option, a battery monitor 112 circuit provides an indication of the level of charge remaining in the battery. As the energy stored in the battery is used by the headset 10, the voltage level will decrease. When the voltage level drops below a predetermined threshold, the headset 10 provides an indication that the energy level in the battery is low. If the batteries 110 are rechargeable, either the entire headset 10 or the batteries 110, removed from the headset, may be placed in a charger to recharge the batteries 110. If the batteries 110 are not rechargeable, they may be replaced.

A proximity sensor 120 may be used to extend the life of the batteries. The proximity sensor 120 is operatively mounted on the earphone 40, 50 to detect when the headset 10 is on a patient's head. The proximity sensor 120 generates a signal indicating that an object (e.g. the patient) is near the earphone 40, 50. The wireless audio module 94 is configurable to operate in a first operating mode or a second operating mode as a function of the signal generated by the proximity sensor 120. In the first operating mode, corresponding to the presence of an object near the proximity sensor 120, the wireless audio module 94 is fully operational. In the second operating mode, corresponding to the absence of an object near the proximity sensor 120, the wireless audio module 94 enters a stand-by state, reducing the overall power consumption of the earphone 40, 50. Optionally, the wireless audio module 94 may remain in the fully operational state for a predetermined time after the signal from the proximity sensor 120 is removed.

The MRI scan room 2 is typically an acoustically noisy environment due to the operation of the MRI scanner. The noise level may be of sufficient magnitude to cause discomfort to the patient while obtaining an MRI image. According to one embodiment of the invention, the inner periphery 72 of the cushion 70 on each earphone 40, 50 is configured to surround a patient's ear canal. The cushion 70, therefore, acts as a passive noise attenuation device, reducing the level of the noise reaching the patient's ear. In addition, each earphone 40, 50 may include active noise cancellation. The active noise cancellation may be included within the wireless audio module 94 or a separate processing device 124 may be included. If a microphone 46 is included for patient communication, that microphone 46 may be sampled to receive signals corresponding to the noise, or audio signals, present in the MRI scan room 2. Optionally, one or more separate microphones 122 may be mounted on the earphone 40, 50 and sampled to receive signals corresponding to the noise, or audio signals, present in the MRI scan room 2. The active noise cancellation module continually monitors the audible signals to determine ambient noise and generates a signal in opposition to the ambient noise. The signal may be, for example, an electronic signal 180 degrees out of phase with the electronic signal representing the ambient noise. The active noise cancellation module then generates an audible signal corresponding to the electronic signal which cancels at least a portion of the ambient noise present in the scan room 2.

The active noise cancellation may be used either to provide comfort to the patient or to facilitate communication with the patient. Patient comfort may be increased by measuring the ambient noise and generating a noise cancelling signal to be reproduced by the speaker 100 of the earphone 40, 50. This signal reduces the level of noise detected by the patient. Communication with the patient is improved by measuring the ambient noise and generating a noise cancelling signal which is added to an audio signal corresponding to the patient's voice. This reduces the level of ambient noise wirelessly transmitted, for example, to the operator in the control room 3 during a scan, making it easier for the operator to understand a patient's response or request.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A magnetic resonance (MR) compatible headset for receiving a radio frequency (RF) audio signal during an MR scan, comprising:
   a first earphone operable to be worn by a patient within a MR scanner during the MR scan, the first earphone including:
      a first housing having at least one opening through a surface located proximate to a first ear canal of the patient when the first earphone is worn by the patient,
      an RF audio module mounted proximate the first housing, such that the RF audio module is located within the MR scanner during the MR scan, the RF audio module configured to receive the RF audio signal and output a wired audio signal,
      a signal processing device configured to receive the wired audio signal and to process the wired audio signal into a first channel signal and a second channel signal, and
      a first speaker mounted within the first housing proximate the at least one opening of the first housing, wherein the first speaker is configured to receive the first channel signal and to reproduce the first channel signal as an audio output;
   a second earphone operable to be worn by the patient within the MR scanner during the MR scan, the second earphone including:
      a second housing having at least one opening through a surface located proximate to a second ear canal of the patient when the second earphone is worn by the patient, and
      a second speaker mounted within the second housing proximate the at least one opening of the second housing, wherein the second speaker is configured to receive the second channel signal and to reproduce the second channel signal as an audio output; and
   a transmission means for transmitting the second channel signal between the signal processing device and the second speaker, wherein each component of the headset is made of materials having a low magnetic signature.

2. The MR compatible headset of claim 1 wherein each component of the headset is made of materials having a low magnetic susceptibility.

3. The MR compatible headset of claim 1 wherein the transmission means includes an electrical conductor connected between the first and second earphones and at least one cable trap connected in series with the electrical conductor, the cable trap configured to reduce currents induced by magnetic fields during the MR scan.

4. The MR compatible headset of claim 1 wherein the transmission means includes a first optical transceiver in the first earphone, a second optical transceiver in the second earphone, and an optical fiber connecting the first and second optical transceivers.

5. The MR compatible headset of claim 1 wherein the transmission means includes a second RF audio module in the second earphone and the RF audio module in the first earphone is configured to retransmit the second channel signal to the second RF audio module.

6. The MR compatible headset of claim 1 wherein:
   the first earphone further includes a proximity sensor having a detection range and configured to generate a signal corresponding to an object present within the detection range; and
   the RF audio module and the signal processing device are configurable to operate in a first operating mode or a second operating mode as a function of the signal generated by the proximity sensor.

7. The MR compatible headset of claim 1 wherein the RF audio signal is a stereo signal having a left and a right channel and the signal processing device separates the left channel into one of the first or second channel signals and separates the right channel into the other of the first or second channel signals.

8. The MR compatible headset of claim 1 wherein:
   the first earphone further includes at least one microphone configured to detect ambient audio signals and generate a first signal corresponding to the ambient audio signals; and
   the signal processing device is further configured to:
      receive the first signal corresponding to the ambient audio signals, generate a second signal that cancels at least a portion of the first signal, and combine the second signal with at least one of the first channel signal and the second channel signal.

9. The MR compatible headset of claim 8 further comprising a microphone configured to receive the patient's voice and transfer a third signal to the signal processing device corresponding to the patient's voice, wherein the signal processing device is further configured to add the second signal to the third signal and to generate a fourth signal resulting from the summation of the second and third signals.

10. The MR compatible headset of claim 1 wherein each of the first and the second earphone is a bud-style earphone, configured to engage a patient's ear canal.

11. The MR compatible headset of claim 1 further comprising:

a support arm having a first end and a second end, the first end of the support arm connected to one of the first earphone or the second earphone; and a microphone mounted proximate the second end of the support arm, wherein the microphone is configured to receive the patient's voice and transfer a signal to the RF audio module and wherein the RF audio module is configured to wirelessly transmit the signal received from the microphone.

12. The MR compatible headset of claim 11 wherein the microphone receives ambient noise along with the patient's voice and the RF audio module is configured to:

process the signal to separate the patient's voice from the ambient noise;

generate an audio signal that cancels at least a portion of the ambient audio signals, and add the audio signal that cancels at least a portion of the ambient audio signals to the signal received from the microphone prior to wirelessly transmitting the signal.

13. The MR compatible headset of claim 1 wherein at least one of the first and second earphones further includes a display unit.

14. A magnetic resonance (MR) compatible headset operable to be worn by a patient within an MR scanner during an MR scan, wherein the MR compatible headset receives a radio frequency (RF) audio signal during the MR scan, the MR compatible headset comprising:

an RF audio module configured to receive the RF audio signal and output a wired audio signal;

a signal processing device configured to receive the wired audio signal and to process the wired audio signal into a first channel signal and a second channel signal;

a first earphone including:

a first housing having at least one opening through a surface located proximate to a first ear canal of the patient when the first earphone is worn by the patient, a first speaker mounted within the first housing proximate the at least one opening of the first housing, wherein the first speaker is configured to receive the first channel signal and to reproduce the first channel signal as an audio output;

a second earphone including:

a second housing having at least one opening through a surface located proximate to a second ear canal of the patient when the second earphone is worn by the patient, and a second speaker mounted within the second housing proximate the at least one opening of the second housing, wherein the second speaker is configured to receive the second channel signal and to reproduce the second channel signal as an audio output;

a first communication connection between the signal processing device and the first speaker for transmitting the first channel signal; and a second communication connection between the signal processing device and the second speaker for transmitting the second channel signal, wherein each component of the headset is made of materials having a low magnetic signature.

15. The MR compatible headset of claim 14 wherein the RF audio module and the signal processing device are each located within the first housing.

16. The MR compatible headset of claim 15 wherein the second communication connection includes an electrical conductor connected between the first and second earphones and at least one cable trap connected in series with the electrical conductor, the cable trap configured to reduce currents induced by magnetic fields during the MR scan.

17. The MR compatible headset of claim 15 wherein the second communication connection includes a first optical transceiver in the first earphone, a second optical transceiver in the second earphone, and an optical fiber connecting the first and second optical transceivers.

18. The MR compatible headset of claim 15 wherein the second communication connection includes a second RF audio module in the second earphone and the RF audio module in the first earphone is configured to retransmit the second channel signal to the second RF audio module.

19. The MR compatible headset of claim 14 wherein:

the first earphone further includes at least one microphone configured to detect ambient audio signals and generate a first signal corresponding to the ambient audio signals; and the signal processing device is further configured to:

receive the first signal corresponding to the ambient audio signals, and generate a second signal that cancels at least a portion of the first signal, and combine the second signal with at least one of the first channel signal and the second channel signal.

20. The MR compatible headset of claim 14 wherein each component of the headset is made of materials having a low magnetic susceptibility.

* * * * *